US005839445A

United States Patent [19]
Kaufman

[11] Patent Number: 5,839,445
[45] Date of Patent: Nov. 24, 1998

[54] METHOD OF DIAGNOSIS OF DISEASES USING CONFOCAL MICROSCOPE

[75] Inventor: Stephen C. Kaufman, New Orleans, La.

[73] Assignee: Con-S Ltd., Metairie, La.

[21] Appl. No.: 686,986

[22] Filed: Jul. 25, 1996

[51] Int. Cl.$^6$ ..................................................... A61B 19/00
[52] U.S. Cl. .......................................... 128/898; 600/300
[58] Field of Search .................................... 128/898, 897; 359/235, 368, 385, 386, 740; 351/221, 206; 250/459.1; 435/6; 356/360; 600/476, 300

[56] References Cited

PUBLICATIONS

"Onychomycosis", (Review Article), *Derm*, Feb., 1972, vol. 105, pp. 263–174, Nardo Zaisa, MD.
"Use of confocal imaging in the study of biological structures", *Applied Optics*, Aug., 1987, vol. 26, No. 16, pp. 3239–3243, W.B. Amos, et al.
"The Morphologic Characteristics of Tumor Blood Vessels as a Marker of Tumor Progression in Primary Human Uveal Melanoma:", *Hum Pathol*, Nov., 1992, vol. 23, No. 11, pp. 1298–1305, Robert Folberg, MD, et al.
"In Vivo Epiluminescence Microscopy: Improvement of Early Diagnosis of Melanoma", *The Journal of Investigative Dermatology, Inc.*, Mar., 1993, vol. 100, No. 3, Issue 0022–202X, p356S362S, Hubert Pehamberger, et al.
"In vivo Vision of the Human Skin with Tandem Scanning Microscope", *Dermatology*, 1993, vol. 186, pp. 50–54, P. Corcuff, et al.
"New Approaches to the Diagnosis and Management of Onychomycosis", *International Journal of Dermatology*, Apr. 1994, vol. 33, No. 4, pp. 292–299, Vincent Barranco, MD.
"Three–dimensional reconstruction of the Meissner corpuscle of man,", *J. Anat.*, 1985, vol. 186, pp. 261–270, P. Castano, et al.
"Mycology of nail disorders", *Journal of Amer. Acad. of Derm.*, Sep. 1994, vol. 31, No. 3, pt 2, pp. S68–S74, Gillian Midgley, PhD, et al.
"Diagnostic Microscopique Des Onychomycoses", *Ann. Dermatol. Venereol.*, 1994, vol. 121, pp. 25–29, G.E. Piérard, et al.
"Academy 95", *Amer. Acad. of Derm*, Jul., 1995, Program and Poster Exhibits, p. 51–with attachments that were unpublished.
"Clinical Pearl: Diagnosis of onychomycosis, Pearls of Wisdom", *Amer. Acad. of Derm*, 1995, vol. 32, No. 3, pp. 500–501, Boni e. Elewski, MD.
"Confocal microscopy: A new tool for the study of nail unit", *Amer. Acad. of Derm*, Apr., 1995, vol. 32, No. 4, pp. 668–669, Stephen C. Kaufman, MD, et al.
"In Vivo Confocal Scanning Laser Microscopy of Human Skin", *Journal of Investigative Dermatology, Inc.*, Jun., 1995, vol. 104, No. 6, pp. 946–952, Milind Rajadhyaksha, et al.

*Primary Examiner*—Mickey Yu
*Assistant Examiner*—Kelly O'Hara
*Attorney, Agent, or Firm*—Burns, Doane, Swecker & Mathis, L.L.P.

[57] ABSTRACT

A method of diagnosing a disease of a fingernail, a toenail, the skin, or a mucus membrane using a confocal microscope to observe abnormal structures within the fingernail, the toenail, the skin, or the mucus membrane respectively and comparing the characteristics of those structures to corresponding characteristics structures known to be associated with a disease state is taught herein. A method of monitoring the progress of a treatment of a diseases of a fingernail, a toenail, the skin, or a mucus membrane using a confocal microscope to observe changes over time of an infected area is also taught.

1 Claim, No Drawings

METHOD OF DIAGNOSIS OF DISEASES USING CONFOCAL MICROSCOPE

BACKGROUND

The present invention relates to methods for diagnosing diseases of fingernails, toenails, skin, and mucus membranes using a confocal microscope and monitoring the treatment of those diseases using a confocal microscope.

Diseases of fingernails and toenails are common and as many as 20% of the cases of such diseases are thought to be of mycotic, i.e., fungal, origin. Mycotic infection of the nails, termed "onychomycosis," exists as four clinical types distinguished by apparently unique host-parasite relationships (see Zaias, N., Arch. Derm., vol 105, 283(1972)). Although dermatophytes are the most common pathogen, Candida, a yeast, is also frequently identified.

It has often been difficult to determine if a diseased nail was a case of onychomycosis and if so, what fungus was the cause. The most common diagnostic procedure in current use for onychomycosis is the potassium hydroxide (KOH) preparation and culture test (Eleweski, *Boni Journal of the American Academy of Dermatology*, vol. 32, No. 3, 500 (1995)). This procedure involves obtaining a specimen of the pathogen, i.e., the fungus, usually by scraping or cutting off a portion of the infected nail. In patients with distal subungual onychomycosis, where the pathogen has invaded the nail bed, removal of most or all of the nail may be required. The specimen is then treated with a KOH solution (e.g., 15% to 20% KOH in dimethyl sulfoxide) to dissolve keratin in the nail material leaving the fungus intact. The fungus may then be identified by examination with a conventional white-light, low-power microscope using an appropriate stain such as chlorazol black E. Alternatively, a specimen may be cultured on a series of standard media, such as agar, each containing a different antifungal agent. This procedure is useful in determining the agent for treatment.

Removal of even a small part of a fingernail or toenail is not only painful, but presents an opportunity for bacterial infection. Further, the growth of a new nail is slow, and the new nail may be deformed and cosmetically unattractive. Both the KOH preparation—direct examination technique and the alternative culture technique often give false readings. Nail biopsy, which also requires removal of a portion of the nail, is painful, expensive, time consuming, and generally is viewed as the last resort.

None of the techniques in current use allow for practical monitoring of the progress of treatment after the fungus has been identified and the appropriate medication has been prescribed. Thus, there is a need for a quick, non-invasive, and economical way to diagnose fungal infections of nails and monitor treatment once the pathogen has been identified.

Standard, incident light microscopy is of little value for viewing the interior of a nail because of the high reflective properties of the keratinized surface of the nail plate. A confocal microscope has the ability to focus the illuminating light and the focal plane of the microscope objective on the same point. This ability enables a confocal microscope to eliminate the spurious reflections of superficial structures of the nail and to focus on the deeper layer of the nail plate and nail bed in vivo.

A confocal microscope typically produces a diffraction-limited light spot that illuminates and scans the subject. Rather than move the subject through a stationary light spot, one of several types of confocal microscopes includes a spinning, perforated disk, called a Nipkow disk, the effect of which is to scan the subject. This and other aspects of confocal microscopes are described in U.S. Pat. Nos. 5,032,720 to White; 5,067,805 to Corle et al.; 5,162,941 to Favro et al.; and 5,177,512 to Abe et al. Both scanning laser confocal microscopes and white-light confocal microscopes are available. General aspects of confocal microscopes are described in J. W. Lichtman, "Confocal Microscopy, " *Scientific American* vol. 271, No. 2, 40–45 (1994). Amos, W. B., et al., *Applied Optics*, vol.26, No.16, 3239 (1987) discuss the use of confocal imaging in the study of biological structures. Kaufman, S. C., et al., *J. Am. Acad. Dern.*, vol. 32, No.4, 668 (1995) have reported the use of a white-light confocal microscope to study the anatomy of the nail including the nail plate and the arterial loops of the nailfold. G. E. Pierard, et al., *Ann. Dermatol. Venereol.*, vol. 121, 25–29 (1994), suggested that confocal microscopy was a technique of the future for dermatology.

It is an object of the present invention to provide a method of diagnosis of diseases of fingernails, toenails, skin and mucus membranes by visual examination of the internal parts of a fingernails, toenails, skin and mucus membranes respectively with a confocal microscope. Another object is to provide a quick, nonintrusive and substantially painless method of monitoring the treatment of a disease of the fingernails, toenails, skin and mucus membranes.

SUMMARY

A first aspect of the present invention is a method of diagnosing a disease in a nail comprising the following steps:

a) placing the nail within the effective viewing area of a confocal microscope;

b) placing an optical coupling medium between the lens of the confocal microscope and the surface of the nail;

c) using the confocal microscope to scan at one or more levels below the surface of the nail for structures not observed in a normal nail; and d) comparing the visual characteristics of structures observed with corresponding visual characteristics of structures known to be associated with a disease; and e) where the characteristics of an observed structure substantially match the characteristics of a structure known to be associated with a disease, concluding that the disease in the nail is the disease known to be associated with the structure observed.

A second aspect of the present invention is a method of monitoring treatment of a disease state in a nail comprising the following steps:

a) placing the nail undergoing treatment within the effective viewing area of a confocal microscope;

b) placing an optical coupling medium between the lens of the confocal microscope and the surface nail;

c) using the confocal microscope to observe at one or more levels below the surface of the nail one or more structures associated with the disease being treated;

d) repeating step c at a later period and comparing the visual characteristics of the structures associated with the disease being treated with corresponding visual characteristics of those same structures observed during an early period during the treatment; and e) repeating step d at intervals over the course of the treatment.

DETAILED DESCRIPTION

As used herein the general term "nail" means the nail plate and the nail bed of a fingernail or a toenail. As used herein the term "nail plate" means the hard, keratinized, visible part of a nail. The term "nail bed" means the portion of the nail which is soft, spongy, and lies below and is attached to the nail plate.

Confocal microscopes vary in configuration and location of components, but for purposes of this invention all function in a similar manner. In a typical confocal microscope light is directed through a set of holes in a disk, i.e., a Nipkow disk. As the disk spins, the holes that are illuminated produce a scanning pattern similar to that produced by the electron gun of a television tube. Optically the holes act as pinholes and permit only parallel rays of light to pass. The light that exits the pinholes passes through an objective lens and into the tissue. Light reflected from the tissue passes back through the objective lens and the pinholes and may be collected by a video camera. The image captured by the video camera can be digitized, computer enhanced, and viewed on a video monitor, stored in a digital or analog form, and/or printed on paper.

The depth to which the confocal microscope can optically penetrate to permit in vivo observation in real time is limited only by the light penetration into the tissue and the reflective properties of the structures being observed. One skilled in confocal microscopy will recognize that the structures must reflect some light to be visible. Only the light reflected from the biologic structures at the selected plane is allowed to pass into the image plane and to contribute to image formation. Because both the light and the microscope objective are focused at the same specific focal plane, objects and structures above and below the plane do not interfere with the formed image.

Keratinized nails present a particular problem because of the high, reflective characteristics their surfaces. However, this problem is effectively overcome by placing a viscous optical coupler between the tissue to be viewed and the objective. Suitable optical couplers have a refractive index substantially equal to that of the microscope's objective lens and include, but are not limited to, hydroxypropyl methylcellulose, glycerin, and water.

Typically, before using the diagnostic method of the present invention, a physician would have reason to suspect a disease of a fingernail or toenail in a patient. (For simplicity, the term "physician" is used herein to represent all heath care professionals and researchers who might use the diagnostic method of the present invention.) For example, the nail in question might have a dark cast, be discolored, be cracked, be brittle, be thickened, be growing in an abnormal way, or be causing the patient discomfort. However, the diagnostic method of the present invention could also be used in routine screening examinations because it is quick, noninvasive and relatively low in cost.

A finger or toe bearing a nail to be diagnosed for disease is placed on a stable platform or similar stage to properly position the nail and restrain movement of the finger or toe. The patient is made as comfortable as possible during the diagnosis. The objective lens of a confocal microscope is brought close to the surface of the nail to be diagnosed but the objective lens preferably does not touch the surface. Preferably an optical coupler is place between the objective and the surface of the nail.

The surface of the nail is incrementally scanned with the confocal microscope while keeping the surface of the nail in focus. Observation by the physician is typically via a video monitor receiving computer enhanced images from a video camera of the confocal microscope. If the confocal microscope monitoring system includes a video printer, the examining physician can conveniently print the video images of interest for detail study at a latter date.

After the physician has viewed the surface of the nail to his or her satisfaction, the objective lens may be adjusted so that the focal plane is just below the surface of the nail. The physician may then continue to conduct a systematic scan for structures indicative of a disease state. The physician may then choose to incrementally adjust the objective to scan at a deeper level into the nail. The physician may continue to scan at progressively deeper levels within the nail. Alternatively, the physician may select a small area of the nail and examine the region under that area at several levels, i.e., vertical scan, before doing the same procedure at another area. Typically, the physician would scan by levels until an abnormal structure was discovered, then shift to a vertical scan to better observe the characteristics of the abnormal structure.

The physician compares the visual characteristics of an observed abnormal structure with corresponding visual characteristics of known structures associated with a disease. Where the visual characteristics of the observed structure and those of a structure known to be associated with a disease substantially match, the physician diagnoses the disease of the nail in question to be the same as the disease associated with the structure observed. For example, during an examination of a nail (suspected of having a disease) using a confocal microscope as taught hereinabove, a physician observes a structure having the type of filaments known to the physician and others skilled in the art of dermatology as characteristic of the fungus Trichophyton rubrum (see Midgley, G., et al. *Journal of the American Academy of Dermatology,* vol. 31, No. 3, S68 (1994)). The physician then diagnoses the disease as onychomycosis and prescribes treatment accordingly.

The methods taught hereinabove are readily adaptable to diagnosis of psoriatic disease of the nail. Thus, the first aspect of the present invention includes a method of diagnosing psoriatic disease of the nail comprising the following steps:

a) placing the nail within the effective viewing area of a confocal microscope;
b) placing an optical coupling medium between the lens of the confocal microscope and the surface of the nail;
c) using the confocal microscope to scan at one or more levels below the surface of the nail for structures not observed in a normal nail; and
d) comparing the visual characteristics of structures observed with corresponding visual characteristics of structures known to be associated psoriatic disease of the nail, e.g., the increase presence of whole and fragmented nuclei in superficial layers of the nail. Diminution of whole nuclei and nuclear fragments over a time period indicates remission of the psoriatic disease or a positive treatment result.

The present method of diagnosis is particularly useful for detecting mycotic infections, i.e., onychomycosis. Diseases of the nails other than onychomycosis often are difficult to diagnosis on the basis on visual observation. Nonetheless, it is a significant advantage to know that the disease in question is, or is not, onychomycosis. Further, if the physician diagnoses onychomycosis, in many cases it is possible to determine which fungus is the infecting agent. The present method of diagnosis may be used to diagnose psorias.

Once the cause of a disease of a nail has been determined, a physician is able to prescribe appropriate medication and treatment. This is particularly true for onychomycosis because of the availability of effective antifungal agents. As with most medications, it is important to conscientiously continue a treatment with an antifungal agent until the disease is eradicated or the attending physician determines the treatment is not effective. Therefore, it is a significant advantage for the physician to have a method for easily monitoring the progress of the prescribed treatment. The second aspect of the present invention offers such a method of monitoring.

After a diagnosis of a disease of a fingernail or toenail has been made, and a treatment has been prescribed, the physician records the extent of the disease before treatment begins. At some interval after the treatment has begun, the physician uses the diagnostic method described above to again determine the extent of the disease and compares it to his or her observation before the treatment started. Such observations are continued periodically to determine when treatment can be stopped or should be changed. For example, if a diagnosis is infection by Trichophyton rubrum and physician prescribes a broad spectrum antifungal agent as a treatment, it would be desirable to observe the extent of the infection every other day.

The present method of monitoring the effectiveness of treatment is a distinct advance in the art of treating diseases of the nail. Even if diagnosis can be made using the culture technique, that technique is too slow and too invasive to be used to monitor the progress of treatment.

The methods taught hereinabove are readily adaptable to diagnosis of diseases of the skin such as cancer, psorias, infections and immunologic diseases. Thus, the first aspect of the present invention includes a method of diagnosing disease of the skin of a patient comprising the following steps:
a) placing the skin within the effective viewing area of a confocal microscope;
b) placing an optical coupling medium between the lens of the confocal microscope and the surface of the skin;
c) using the confocal microscope to scan at one or more levels below the surface of the skin for structures not observed in a normal skin; and
d) comparing the visual characteristics of structures observed with corresponding visual characteristics of structures known to be associated with a disease; and
e) where the characteristics of an observed structure substantially match the characteristics of a structure known to be associated with a disease, concluding that the disease in the skin is the disease known to be associated with the structure observed.

One skilled in the art will appreciate that the methods of diagnosis and treatment monitoring of the present invention are applicable to visualizing abnormalities and diseases of a mucus membrane. For example, the method of the present invention can be used to diagnose abnormalities of the conjunctival mucosa of the eye, the oral mucosa of the mouth and cervical mucosa. In the case of the mucus membranes the abnormalities include but are not limited to cancer, infections, and immunological disease. The method of diagnosis of disease of the mucus membranes is substantially the same as diagnosis of disease of the nails taught hereinabove. Thus, a method of diagnosing a disease in a mucus membrane comprising the following steps:
a) placing the mucus membrane within the effective viewing area of a confocal microscope;
b) placing an optical coupling medium between the lens of the confocal microscope and the surface of the mucus membrane;
c) using the confocal microscope to scan at one or more levels below the surface of the mucus membrane for structures not observed in a normal mucus membrane; and
d) comparing the visual characteristics of structures observed with corresponding visual characteristics of structures known to be associated with a disease; and
e) where the characteristics of an observed structure substantially match the characteristics of a structure known to be associated with a disease, concluding that the disease in the mucus membrane is the disease known to be associated with the structure observed.

Likewise, the method of monitoring the effectiveness of treatment of a disease of the skin or mucus membrane is substantially the same as taught hereinabove for a disease of the nails. One skilled in the art would appreciate that only minor adaptation might be need.

The following examples are offered as illustrations of the present invention and are not to be construed a limitation thereof.

EXAMPLES

Example 1. Diagnosis of a Fingernail with a Confocal Microscope

Ten patients with dystrophic fingernails, randomly selected from the Louisiana State University Dermatology clinic, consented to participate in studies of the diagnostic method of the present invention. Nail cultures were done on each patient and the present method of diagnosis using a confocal microscope was done seven to 21 days later. A determination of the nature of the dystrophy made before the results of the nail cultures were known.

The confocal microscope used in this study has a single-sided Nipkow disk and is described in copending U.S. Pat. application No. 08/687,287 by Miroslav Maly et al., filed on Jul. 25, 1996, entitled "Scanning Confocal Microscope", incorporated herein by reference. The illumination from a 100 W mercury lamp (Nikon, Tokyo, Japan) is brought to the microscope by a fiber-optic bundle (Dolan-Jenner, Lawrence, Mass.). The spectrum of the light has the greatest intensity through the visible range. Illumination of the nails is limited to only 2% of the incoming light by the spinning disk. The contact tip of the microscope is a modified special objective lens (BioOptics, Boston, Mass.). There is no direct contact between the objective and the nail, because the objective lens actually rides on a layer of the coupling medium (methyl cellulose). The incident beam does not produce any sensation of warming on the nail; in this study the procedure was accomplished with no reported sensation caused by the beam. The high-resolution images thus formed are directed to a high-resolution, low-light video camera (video Scope, Washington, D.C.) and stored on super-VHS videotape. The images can also be directed to an IBM-compatible 486 or Pentium (trademark) computer for processing with image analysis software (Optimas, Bioscan Inc., Seattle, Wash.) and viewing on a high-resolution Sony monitor.

The patients' hands were placed on a platform so that the fingernails could be stabilized while being observed with the confocal microscope. A 20X specular objective of the confocal microscope was brought close to the fingernail but not in contact with it. A drop of hydroxypropyl methylcellulose solution (IOLAB Pharmaceuticals, Claremont, Calif.) as an optical coupling agent was placed between the objective and the surface of the nail. Images of the suspected areas of mycotic infection were captured at approximately 0.1 to 0.5 mm intervals below the surface of the nail. The captured images were printed and resulting photographs compared in detail to similar photographs of known fungi. Where there was a visual match of characteristics of the fungus being studied and of characteristics of a known fungus the diagnosis was that the infection was the known fungus. Where there was no match, no diagnosis was recorded.

Four of the ten patients studied were culture-positive for Candida albicans and the present diagnostic method could correctly identify the blastospores and pseudohyphae of Candida albicans in each of these patients. Three of the patients were culture-positive for the dermatophyte, Trichophyton rubrum. For two of these patients, branching hyphae were clearly visible on confocal microscope examination. This finding is consistent with a dermatophyte infection. However, no fungal structures were visible within the fingernails of patient five. The remaining three patients were culture-negative for fungi and no diagnosis could be made with confocal microscopy.

The dermatophytes within a nail were easily identified, because the hyper-reflective, branching hyphal filaments traversed the substance of the nail in a plane that was parallel to the nail's surface. Candida albicans were slightly more difficult to identify within the nail because the blastospores and pseudohyphae appeared to travel in a pattern that was primarily perpendicular to the surface of the nail. This type of "head on" view from the confocal microscope is not typically seen with other types of microscopy. However, the differential growth pattern between Trichophyton rubrum and Candida albicans was useful in distinguishing between these two common pathogens in onychomycosis.

Example 2. Monitoring Treatment of a Disease of a Fingernail with a Confocal Microscope A patient having a diseased fingernail previously diagnosed as infected by Trichophyton rubrum is starting a prescribed treatment of Sporanox (trademark) 400 mg daily for one week per month repeated for four months. The patient's diseased fingernail is prepared and examined by an attending physician with a confocal microscope in a similar manner as described in Example 1. The extent of the infection is observed by a physician and the images appearing on the video monitor are recorded in digital form on a conventional floppy disk.

After three days of the treatment, the patient's infected fingernail again is observed in a manner substantially the same as at the start of the treatment. A third observation, substantially the same as the second, is conducted six days after the start of the treatment. Comparing the recorded images of the first, second, and third observations, the attending physician concludes that the prescribed treatment is effective because the size of the infected area is diminishing. Based on the rate of change of the area of infection, the physician predicts a date when the treatment should be complete and the infection eradicated. On or after the predicted date of eradication, the physician again observes the nail in question and determines if, indeed, the infection is eradicated or if further treatment is indicated.

I claim:

1. A method of diagnosing disease in a mucus membrane comprising the following steps:
   a) placing in vivo the mucus membrane within the effective viewing area of a confocal microscope;
   b) placing an optical coupling medium between the lens of the confocal microscope and the surface of the mucus membrane;
   c) using the confocal microscope to scan at one or more levels below the surface of the mucus membrane for structures not observed in a normal mucus membrane; and
   d) comparing the visual characteristics of structures observed with corresponding visual characteristics of structures known to be associated with a disease; and
   e) where the characteristics of an observed structure substantially match the characteristics of a structure known to be associated with a disease, concluding that the disease in the mucus membrane is the disease known to be associated with the structure observed.

* * * * *